United States Patent
Laitinen et al.

(10) Patent No.: US 6,995,021 B2
(45) Date of Patent: Feb. 7, 2006

(54) METHOD AND APPARATUS FOR QUALITATIVE AND QUANTITATIVE DETECTION OF ANALYTES

(75) Inventors: Mika Laitinen, Jyväskylä (FI); Jukka Pekola, Jyväskylä (FI); Jari Salmela, Jyväskylä (FI); Matti Vuento, Helsinki (FI)

(73) Assignee: Magnasense Oy, Jyvaskyla (FI)

( * ) Notice: Subject to any disclaimer, the term of this patent is extended or adjusted under 35 U.S.C. 154(b) by 0 days.

(21) Appl. No.: 10/478,160

(22) PCT Filed: Jun. 19, 2002

(86) PCT No.: PCT/FI02/00539

§ 371 (c)(1),
(2), (4) Date: Nov. 19, 2003

(87) PCT Pub. No.: WO02/103346

PCT Pub. Date: Dec. 27, 2002

(65) Prior Publication Data

US 2004/0171172 A1    Sep. 2, 2004

(30) Foreign Application Priority Data

Jun. 19, 2001    (FI) .................................. 20015015

(51) Int. Cl.
*G01N 25/18*    (2006.01)

(52) U.S. Cl. ................ 436/149; 422/82.01; 422/82.02; 436/518; 436/526; 324/228; 324/200; 324/207.15

(58) Field of Classification Search ................ 435/4, 435/7.1, 283.1; 436/518, 524, 525, 526, 436/43, 149, 806; 422/50, 68.1, 82.01, 82.02; 324/228–263, 200, 207.11, 207.15
See application file for complete search history.

(56) References Cited

U.S. PATENT DOCUMENTS

| | | | |
|---|---|---|---|
| 3,433,057 A | | 3/1969 | Halsey .................... 73/61.71 |
| 5,001,424 A | * | 3/1991 | Kellett et al. ............... 324/204 |
| 5,078,010 A | * | 1/1992 | Lock ......................... 73/304 R |
| 5,315,243 A | | 5/1994 | Kempster et al. ........... 324/204 |
| 5,537,037 A | | 7/1996 | Otaka et al. ................ 324/240 |
| 5,554,932 A | * | 9/1996 | Jeffers ........................ 324/204 |
| 5,793,199 A | * | 8/1998 | Kasahara et al. ........... 324/204 |
| 6,045,585 A | * | 4/2000 | Blainey ....................... 717/156 |
| 6,110,660 A | * | 8/2000 | Kriz et al. ..................... 435/4 |
| 6,123,902 A | * | 9/2000 | Koch et al. ................... 422/50 |
| 6,437,563 B1 | | 8/2002 | Simmonds et al. |
| 2003/0027197 A1 | * | 2/2003 | Nikitin et al. ................. 435/6 |

FOREIGN PATENT DOCUMENTS

| | | |
|---|---|---|
| EP | 0773440 | 8/1996 |
| JP | 2000097941 | 4/2000 |

* cited by examiner

*Primary Examiner*—Long V. Le
*Assistant Examiner*—Melanie Yu
(74) *Attorney, Agent, or Firm*—Fildes & Outland, P.C.

(57) ABSTRACT

A method and apparatus for the qualitative and quantitative detection of analytes is disclosed in which in the detection of an analyte in a sample, an elongated migration base is used, in which there is an area for binding a magnetically marked analyte, and in which, in stages
the sample is absorbed into the migration base and
the sample spreads on the migration base into the area.
The elongated migration base is arranged in connection with a coil and a change in inductance, correlating with the content of the magnetically marked analyte, is detected.

4 Claims, 5 Drawing Sheets

METHOD AND APPARATUS FOR QUALITATIVE AND QUANTITATIVE DETECTION OF ANALYTES

TECHNICAL FIELD

The present invention relates to a method and apparatus for the qualitative and quantitative detection of analytes, in which, in the detection of an analyte in a sample, an elongated migration base is used, in which there is an area for binding a magnetically marked analyte, and in which, in stages
   the sample is absorbed into the migration base and
   the sample spreads on the migration base to the said area.

BACKGROUND OF THE INVENTION

Diagnostic tests, which are performed outside a normal laboratory environment and often without special instruments, have over the past few years become extremely important. Many of these tests, for example, detecting the presence of choriongonadotropin in urine in order to detect pregnancy, are in the nature of rapid immunological tests.

In recent years, the immunochromatographic test in particular has become a means of rapid immunological diagnostics. This method is characterized by the use of a porous material, such as nitrocellulose attached to a plastic film, as a medium, to which a narrow detection zone of biochemically active binder reagents are attached by absorption or in some other way. As the test proceeds, the binder reagent binds moving analytes driven by the capillary forces in the medium.

Known immunoassay methods can be roughly divided into two main types. In the so-called sandwich type, the analyte to be measured is sandwiched as a detection zone between two specific binder molecules, one of which is attached to a solid material and the other is marked with a radioactive, fluorescent, coloured, or other marker. There can be one or several detection zones. Both of the binder reagents are usually biochemically antibodies.

The analyte contained in the sample is detected by bringing the sample into contact with the detection zone together with a marked binder reagent that is also analysis specific, in which case the analyte forms a layer on the detection zone between the binder reagent attached to the detection zone and the marked binder reagent (the 'sandwich principle'). The marked binder reagent may be coloured, which can be achieved by marking the binder reagent with microparticles, or with a colloidal metallic or non-metallic salt.

In the so-called competitive type of assay, the marked analyte competes with an analyte contained in the sample, for binding with a binder reagent. In this system, the amount of the measured marker bound in the binder reagent is inversely proportional to the amount of the analyte contained in the sample.

A third main type, so-called homogeneous assay, is represented by homogeneous enzyme-immunoassay, which is disclosed in the patent publication U.S. Pat. No. 3,817,834. Another technique, exploiting a steric hindrance, is Steric Hindrance Enzyme Immunoassay (SHEIA). In this method too, the analyte weakens, instead of amplifying, the signal being measured. As such, the use of a porous matrix as a migration base and the attachment of a specific binding reagent, such as an antibody, to it, was known already in the 1980s.

The interpretation of the results of such tests is generally based on the visual examination of the migration base, for example, in the pregnancy test, the observation, against the migration base, of the line that forms. In some tests, the visual effect that arises is so weak that photometric devices must be used to examine it. It is difficult to convert these assay results into an electronic form for further analysis.

Antibodies marked with magnetic particles are widely used in immunographic assay. The known apparatuses for detecting them are bridge-type solutions, in which a coil is used to examine the magnetic force emitted by the analyte on the migration base. U.S. Pat. No. 6,110,660 discloses an apparatus of this type, which, however, has a complicated circuit.

In the patent literature, reference to the use of magnetic particles in immunoassay is also made in patent publications such as U.S. Pat. Nos. 4,628,037, 5,252,493, 5,238,811, 5,993,740, 6,046,585, 6,150,181, and EP-386690A1. In the method of publication U.S. Pat. No. 6,046,585, a sample of the analyte forms a magnetic dipole, in which a varying magnetic field is induced by means of an excitation signal. The ends of the dipole form their own electrical fields, which are detected by means of detector coils and electronics connected to them.

To date, immunochromatography tests have been mainly applied to the detection of protein analytes. These are relatively large molecules, for the detection of which a test operating on the sandwich principle described above is suitable. However, the molecular size of many interesting analytes, such as steroids, pharmaceuticals, pesticides, etc., is so small that the sandwich principle cannot generally be applied to their detection. The competitive principle has been used to assay such analytes.

SUMMARY OF THE INVENTION

The present invention is intended to create a method and apparatus, by means of which it is possible to perform rapid and precise immunoassays, which are traditionally held to include, for example radio immunoassay (RIA), enzyme immunoassay (EIA), and fluoro-immunoassay. The industrial field of application of the invention is in diagnostics, in which reagent kits exploiting the method and apparatus according to the invention can be manufactured, especially for use in immunological rapid tests, in which assay is performed rapidly.

The characteristic features of the method for the qualitative and quantitative detection of analytes, in which in the detection of an analyte in a sample, an elongated migration base is used, in which there is an area for binding a magnetically marked analyte, and in which, in stages
   the sample is absorbed into the migration base and
   the sample spreads on the migration base into the said area, is characterized in that the elongated migration base is arranged in connection with a coil and a change in inductance, correlating with the content of the magnetically marked analyte, is detected.

The characteristic features of the apparatus for the qualitative and quantitative detection of analytes, in which a magnetically marked analyte absorbed into a migration base is arranged to be detected with the aid of coil devices which include,
   primary coil devices
   devices for supplying the said coil devices with alternating current,
   secondary coil devices, which include an astatic pair of coils that comprise at least two secondary coils, arranged in connection with the primary coil devices, and devices for observing the state of equilibrium of the said pair of coils, is characterized in that at least one of the secondary coils is arranged to have a shape that will receive the migration base tightly in connection with it. A rapid and accurate detection result is achieved with the aid of the apparatus according to the invention.

The use of the method according to the invention is particularly suitable, for example, for a group of diagnostic tests that have become important in recent years and which are performed outside a laboratory environment, for example, in doctors' surgeries. Some examples, which are in no way exclusive, of the analytes which detection the method according to the invention is suitable for include among others proteins, nucleic acids, peptides, polysaccharides, steroids, pharmaceuticals, pesticides, antibiotics, toxic substances, viruses, yeasts and microbes etc.

The apparatus has a simple construction while, as the assay results are already electronic signals, they can be easily interpreted and further processed. The apparatus is neutral in colour, so that coloured samples do not cause problems in the interpretation of results, as happens in the photometric methods according to the state of the art. According to one preferred embodiment, plate-like or tubular capillaries, by means of which the detection is rapid, can be used as the migration base in the apparatus. The other characteristic features of the invention are stated in the accompanying Claims.

These and other features and advantages of the invention will be more fully understood from the following detailed description of the invention taken together with the accompanying drawings.

DETAILED DESCRIPTION OF THE INVENTION

Figure 1:
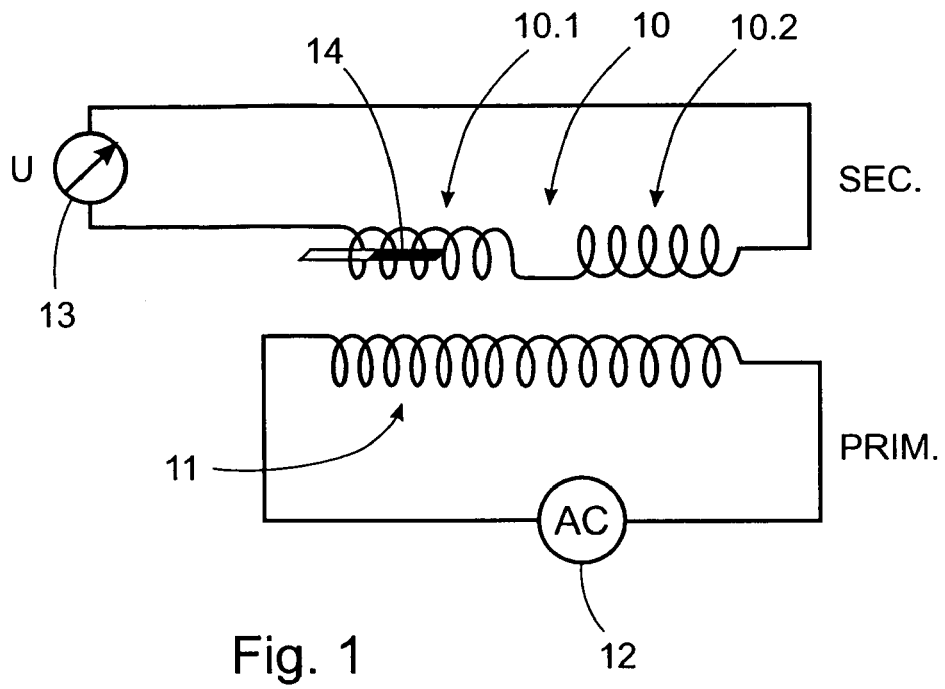
FIG. 1 shows a schematic diagram of the basic construction of the apparatus according to the invention.

FIG. 1 shows the basic construction of the apparatus according to the invention, by means of which rapid immunological assays can be performed. FIG. 1 describes the general operating principle of the apparatus. The apparatus comprises a coil arrangement, which is divided into a primary side (PRI) and a secondary side (SEC).

On the primary side, there is a so-called driver coil 11, to which alternating current (AC) supply devices 12 are connected. On the secondary side, there is a pair of coils 10 connected in series, which comprise coils 10.1 and 10.2. The coils 10.1 and 10.2 are dimensioned in such a way that they have equal inductances. The essential feature of the placing of the receiving coils 10.1, 10.2 is that they are wound in opposite directions. Such a pair of coils 10 can also be called an astatic pair.

In the apparatus according to the invention, the coil 10.1 acts as the so-called receiving coil of the migration base 14 while coil 10.2 acts as its companion. The length of the coils 10.1, 10.2 in the apparatus according to the example is 13 mm. The length of the driver coil 11 in the apparatus according to the example is 58 mm and its length covers the pair of coils 10. The voltage in the receiving pair of coils 10 can be increased by making more wire windings to each unit of length than there are in the driver coil 11.

Figure 3:
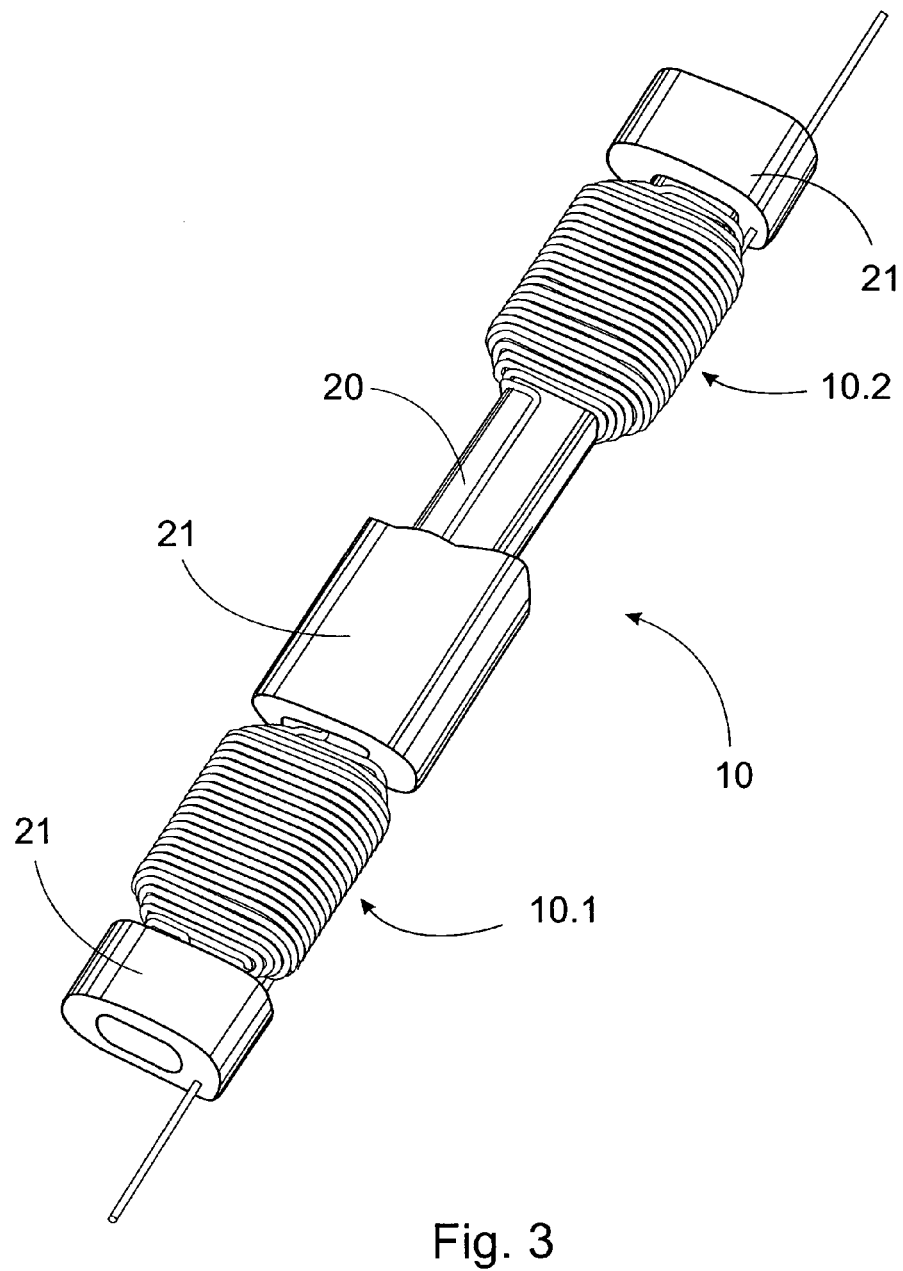
FIG. 3 shows a second embodiment of the apparatus according to the invention, examined at the level of the secondary coil.
Figure 4:
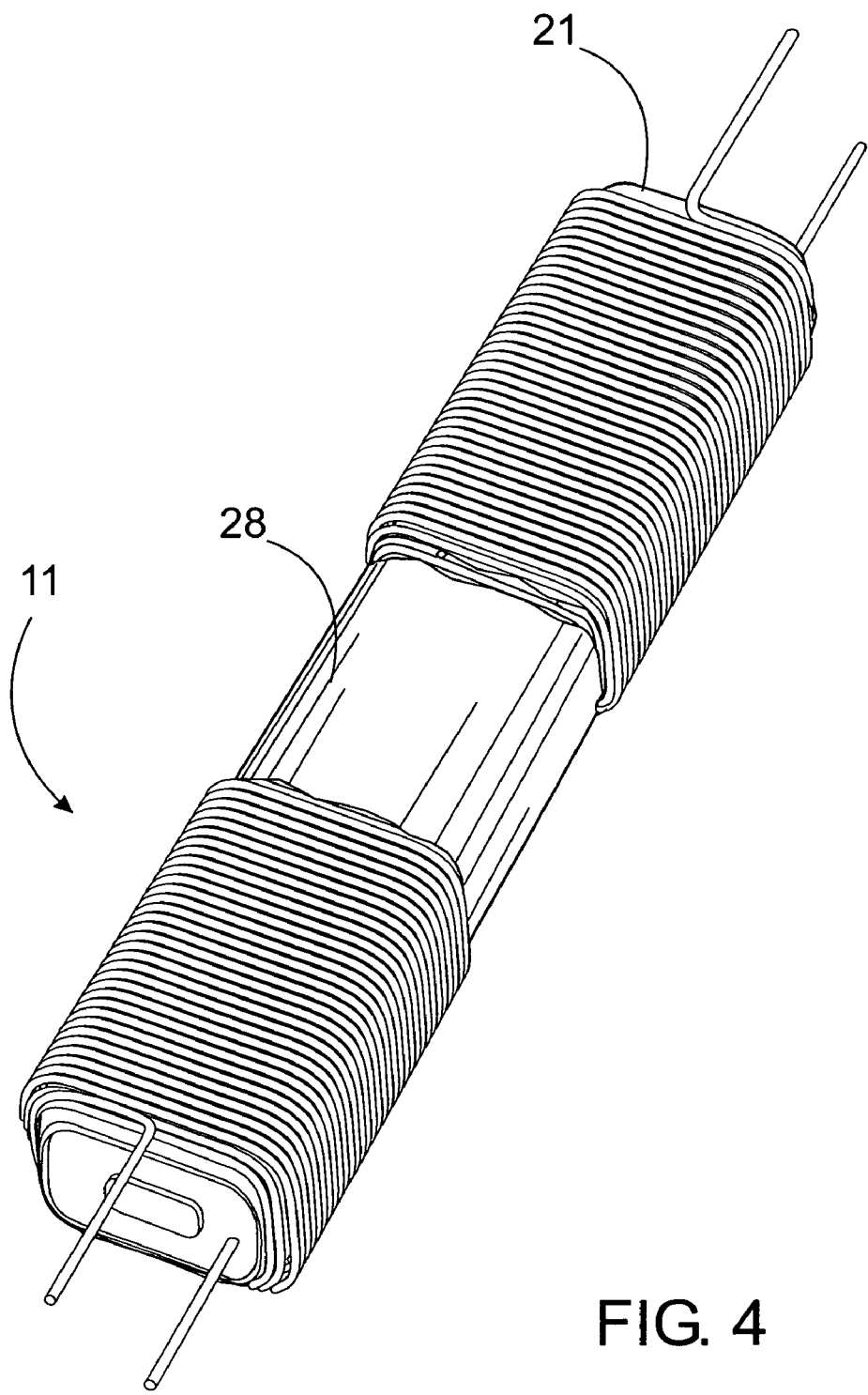
FIG. 4 shows the apparatus of FIG. 3, examined at the level of the primary coil.
Figure 5A:
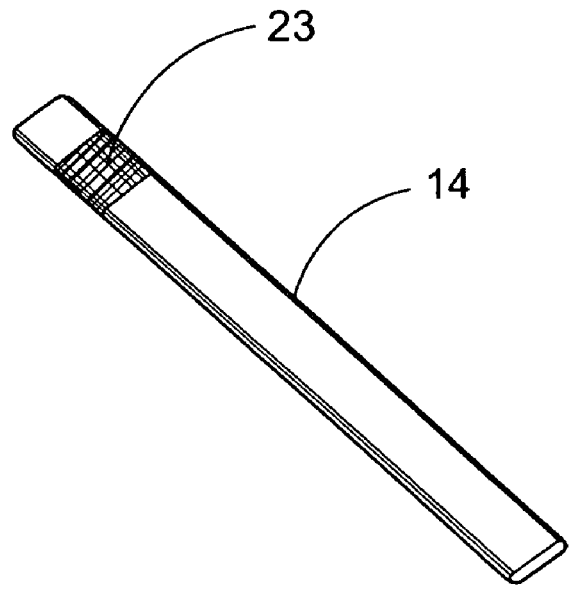
FIG. 5a shows examples of the migration base.
Figure 5B:
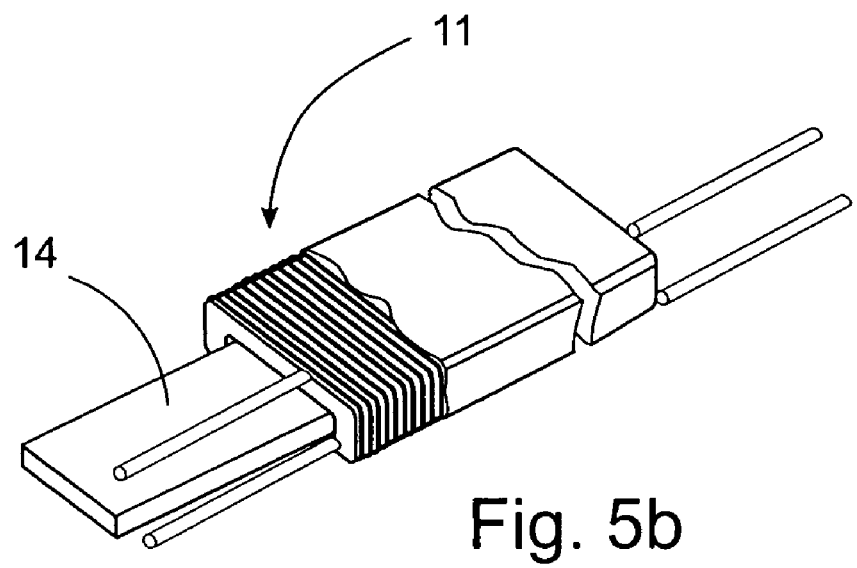
FIG. 5b shows the apparatus according to FIGS. 3 and 4 in the detection situation.

Each secondary-side coil 10.1, 10.2 can also alternatively have its own driver coil, the operating parameters of which and the location of which in relation to the receiving coil 10.1 of the migration base 14 and its companion 10.2 are preferably identical (not shown). A certain amount of non-identicalness can be permitted in the operating parameters and the locations, in which case an electronic circuit compensating for this can be arranged in connection with the apparatus. It is also possible to exploit non-identicality in certain cases, for example, in calibration. It should be noted that the arrangement according to FIG. 1 is a schematic presentation of the real apparatus, an embodiment of which is described later. In reality, the primary and secondary sides can be placed one inside the other, in such a way that the pair of coils 10 of the secondary side is located inside the driver coil 11 acting as the primary side (FIGS. 3, 4, and 5b).

The operating frequency of the driver coil 11, which in the apparatus according to the example is common for both coils 10.1, 10.2 of the secondary pair 10, can be set at, for example, 10 kHz. The frequency depends on, among other factors, the number of windings of the driver coil 11 and it can be adjusted not only using the magnitude of the current, but also using an application (not shown) arranged outside the apparatus.

The secondary pair of coils 10 is connected to a sensitive voltmeter 13, which is used to show the assay result. In place of the voltmeter 13, it is also possible to use a more advanced data collection and analysis device, for example, a computer, by means of which the assay results can be easily recorded and analysed.

Figure 2:
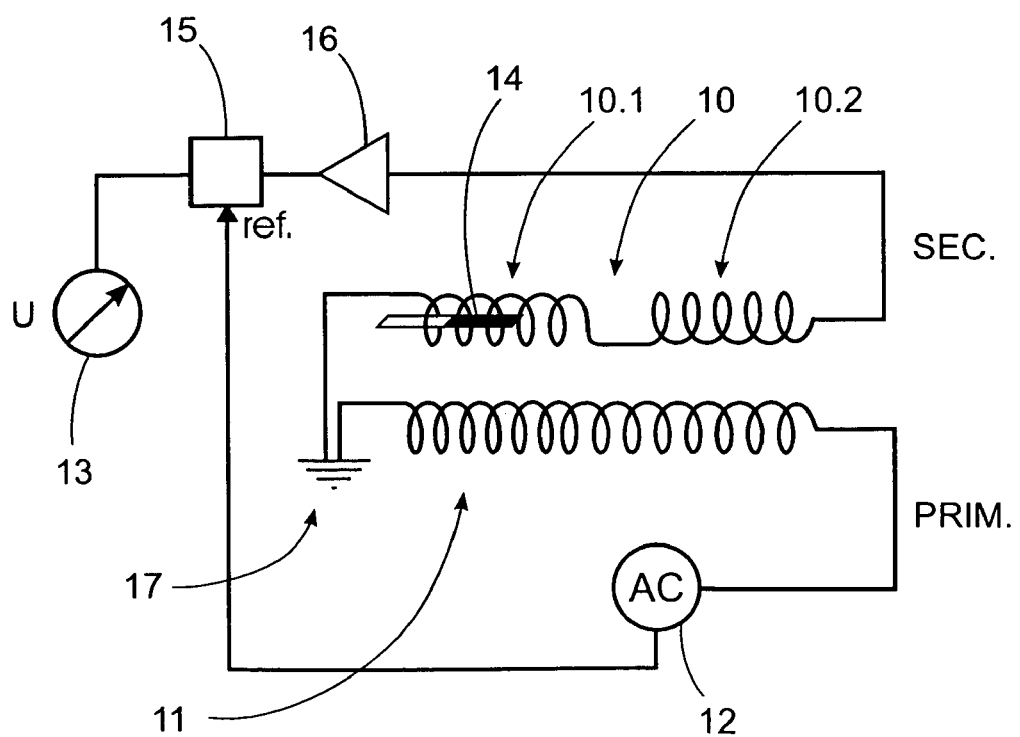
FIG. 2 shows a schematic diagram of a first embodiment of the apparatus according to the invention.

FIG. 2 shows an apparatus according to a preferred embodiment, the basic principles of which are according to FIG. 1. However, a lock-in amplifier 15 has been advantageously added to this between the signal lead coming from the secondary side 10 and the voltmeter.

The reference signal of the lock-in amplifier 15 is taken from the power supply 12 of the driver coil 11 of the primary side. By means of the lock-in amplifier 15, the frequency of the measurement signal is locked to the frequency of the current supplied to the primary side, so that frequency disturbances arising during the operation of the apparatus can be advantageously filtered out. The lock-in amplifier 15 receives the measurement signal through an amplifier 16, by means of which the signal is amplified, in order to make its measurement possible. In addition to the embodiment described, the apparatus may include other electronics that generally assist the assay, as will be known to one versed in the art.

According to the embodiment shown in FIG. 2, the driver coil 11, the pair of coils 10.1, 10.2, and possibly also the migration base 14 may all be connected to the same grounding potential 17. The use of this arrangement is intended to eliminate varying stray capacitances and inductive connections, which may arise inside the coil system.

According to a second preferred embodiment, an grounded 35 conductive area (not shown) can be placed between the driver coil 11 and the pair of coils 10.1, 10.2. According to known transformer technology, this has the effect of reducing stray capacitances and increasing the resonance frequency, thus giving stronger signals. Also other solutions relating to the basic constructions of transformers will be obvious to one versed in the art.

FIGS. 3, 4, and 5b show a second embodiment of the apparatus according to the invention. The inner space of the coil arrangement is shaped advantageously to the shape of the migration base 14, so that it can be fitted tightly inside the coil arrangement. This improves the accuracy of the assay result, because the magnetism arising from the biochemical reactions taking place on the migration base 14 is very weak. The migration base 14 does not necessarily need to be placed inside the coil arrangement, instead, in the assay situation, it can also be close to the coil arrangement.

The coil arrangement is implemented by winding, in the manner shown in FIG. 3, two coils 10.1, 10.2, of identical dimensions, in opposite directions around a tubular body component 20.

The coils 10.1, 10.2 can be located, for example, 5 mm from the ends of the body component 20 and can be, for example, about 13-mm long. The distance between the coils 10.1, 10.2 can be, for example, about 20 mm. The wire used in the coils can be, for example, copper, with a diameter of 0.5 mm. In the coils 10.1, 10.2, there are, for example, slightly more than 20 windings in five layers on top of each other.

After this, pieces 21, for example of some insulating material such as plastic, the outsides of which are shaped like the coils 10.1, 10.2, are fitted around the body component 20.

In FIG. 4, a cover 28 of the same length as the body component 20, and which smooths the coil-arrangement blank to form a uniform tube, is wound on top of the secondary-side pair of coils 10.1, and 10.2, as well as of the pieces 21. On top of this flat surface, the driver coil 11 is wound over the entire length of the body 20.

Next an embodiment is described, in which an hCG (human chorionic gonadotropin, the placenta hormone) assay is performed from urine. The test strip 14 shown in FIG. 5 used as the migration base has pores of nitrocellulose or plastic-coated nitrocellulose, with 12-$\mu$m pores and a thickness of 100 $\mu$m, from which strips 3-mm wide and 50-mm long are cut. Starting 10 mm from the lower end of the strip 14 is a detection zone 23 extending across the strip 14, with a length in the longitudinal direction of the strip 14 of 1 mm. A second antibody, which binds to a different epitope of the hCG than the antibody used in the test reagent, is attached to the detection zone 23 by adsorption.

The attachment takes place by applying 0.24 $\mu$l of the antibody solution (5 mg/ml) per detection zone 23 and allowing the solution to dry. Non-specific binding is prevented by soaking the entire strip 14 in a 3-% BSA solution in a buffer 10 mM PBS pH 7.4, flushing it with the same PBS buffer and drying it in air.

According to a second preferred embodiment, a glass or plastic capillary tube, or two flat surfaces placed against each other, and between which the sample spreads moved by capillary forces, can be used as the sample's migration base 14. When using a capillary tube, the sample enters the area being analysed more rapidly, so that the time required to perform the assay is reduced. The inner surfaces of the capillary tube or plate, which has a diameter of, for example, 1 mm and a length of 10–20 mm, are treated with reagent substances, which are determined by the biochemical nature of the analyte being sought.

The test reagent used in the embodiments is a solution of anti-hCG antibody labelled with 250-nm superparamagnetic particles. The super-paramagnetic particles are coated with the aid of avidin or streptavidin (a technique known to one versed in the art). The test reagent is obtained by mixing 1 ml of super-paramagnetic particles with 1 ml of biotinylated hCG antibody. The mixture is washed five times using a 10 mM PBS pH 7.4+0.1% BSA (bovine serum albumin) buffer and sonicated between washings for 3 s at a power of 4 W/cm$^2$. Finally, the mixture is filtered through a 800-$\mu$m filter.

The antibody is, in turn, biotinylated as follows. The antibody is diluted to a concentration of 1 mg/ml in a buffer of 0.2 M NaHCO$_3$ pH 8.8+0.15 M NaCl. 5 $\mu$l of biotinylating reagent is added to each microliter of the diluted antibody. The biotinylating reagent contains 1 mg of biotinamidocaproate-N-hydroxysuccinimide ester in 50 $\mu$l of N,N'-dimethylformamide. The solution is incubated for 2 hours at room temperature and dialysed three times against a 10 mM PBS pH 7.4 buffer.

The checking of the operating condition and the calibration of the apparatus can be carried out by placing samples absorbed into an elongated migration base 14 one after the other inside the coil 10.1, at least one of the samples being known certainly to be the pure analyte being examined and one having a preferably known content of the analyte being examined. This assay system will give a picture of the linear behaviour of the analyte in question, on the basis of which the apparatus can be calibrated, while also providing additional certainty of the assay result.

The sample used is the urine of the person being tested, 5 $\mu$l of which is mixed with 20 $\mu$l of the test reagent. The mixture is pipetted into a well of a multi-well plate (not shown), into which the test strip 14 is also placed. The test strip 14 is allowed to absorb all the liquid from the well. The test strip may also include a second zone, arranged in connection with the said detection zone 23, to control the spread of the sample on the migration base 14 (not shown).

The following describes the operation of the apparatus according to the invention. The operation of the apparatus is thus based on the phenomenon of mutual inductance, in which the driver coil 11 on the primary side is used to create a unified magnetic field, which induces a current in the secondary-side coils 10.1, 10.2 within the field. Because the coils 10.1, 10.2 within the field are wound in opposite directions, the currents induced in them are also in opposite directions and cancel each other out. The currents and the voltage induced by them depend on the parameters of the driver coil 11 and on the current fed to it and, on the other hand, also on the parameters of the secondary-side coils 10.1, 10.2, such as their dimensions and the number of wire windings wound around them.

FIG. 5b shows a situation, in which the detection zone 23 of the test strip 14 has been brought into contact with the second receiving coil 10.1 and particularly in this case placed inside it. According to one embodiment, a permanent connection (not shown) can also be arranged from the migration base 14 to the coil system. The magnetic particles in the sample, which have reacted in a known biochemical manner in the presence of the analyte, alter the inductance of the receiving coil 10.1, so that the inducing currents of the coils 10.1, 10.2 are of different magnitudes. This difference of the currents is observed as a current running through both coils. The amount of magnetic material brought to the receiving coil 10.1 of the secondary pair 10 can be deduced from the change in the amount of current.

The amount of current can thus also be measured from the voltage produced over the secondary-side pair of coils 10, which is read from a voltmeter 13. The content of an unknown sample can be obtained from the voltage, by comparing the voltage reading obtained with a standard descriptor, created in the calibration stage, of the voltage produced by known hCG samples.

Figure 6:
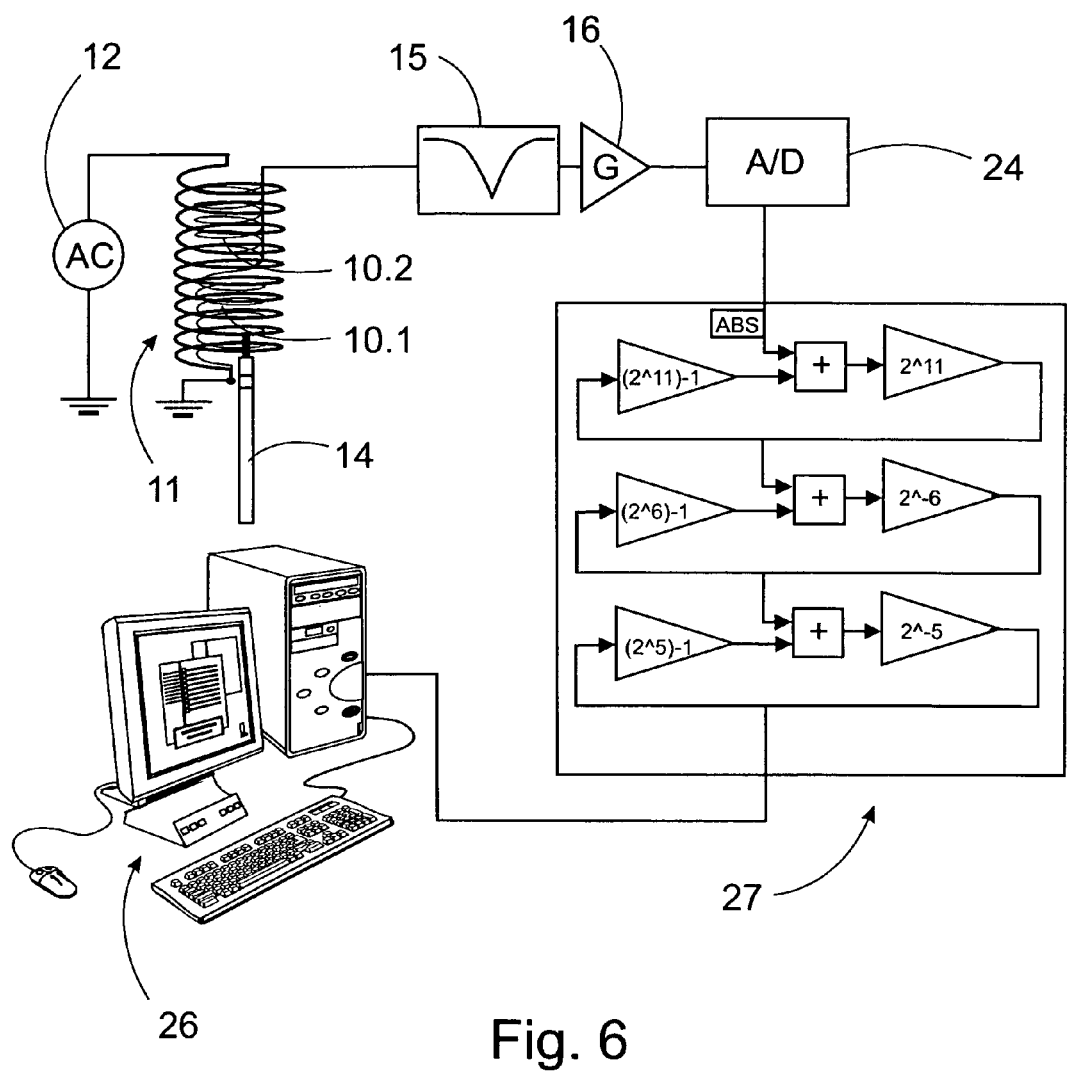
FIG. 6 shows a schematic example of the assay circuit used in the apparatus according to the invention.

FIG. 6 shows a more highly developed embodiment of the assay electronics used in the apparatus according to the invention. In place of the voltmeter 13, it is equally possible to use more developed data-collection devices, such as a PC computer 26, for which the assay results can be advantageously digitalized and recorded for possible further analysis.

Thus, the amount of current can be measured, for example, over the receiving pair of coils 10.1, 10.2. In that case, the apparatus can include, for example, a signal amplifier 16 arranged in connection with the aforementioned lock-in amplifier 15, by means of which all frequencies except the frequency of the signal being examined are first of all filtered out. Next, the signal is converted to digital form using an AD converter 24, permitting further filtering of noise. The use of a digital filter circuit 27 will bring the threshold frequency of the low-pass filtering to close to zero, when interfering noise will be summed out, leaving the signal to be measured. It is possible to read, from the change in the signal, how much magnetic material has been brought to the coil 10.1. As such, the principles of the digital filtering circuit are obvious to one versed in the art, and are not discussed further in this connection.

Because the coils 10.1, 10.2 are set astatically in relation to each other, i.e. they are wound in opposite directions, the voltages induced over them are equal but with opposite signs, due to the identicalness of the coils. The total voltage induced in the pair of coils 10 is thus very small, ideally zero. This automatic zero-indicator property considerably improves the elimination of external disturbances.

In the apparatus according to the invention, the use of an astatic pair of coils 10 makes it also possible to exploit the background compensation principle. The migration base 14 is then pushed inside the receiving pair of coils 10, in such a way that the base 14 protrudes from coil 10.1 into coil 10.2 for the distance that the concentration of particles in the base corresponds to the background (not shown).

According to one embodiment, the apparatus according to the invention can, at least in the case of the driver coil 11 and the receiving pair of coils, be implemented as a planar, essentially two-dimensional, flat construction. One example of an implementation according to such an embodiment is a coil arrangement implemented using a lithographic or similar, for example, layering method. The migration base 14 can then be integrated permanently with the coil system.

When using the apparatus, the assay result is obtained immediately in electronic form, so that, for example, the colour of the sample (for instance, in the case of blood) does not cause problems in interpretation, as may happen in photometric assay.

It should be understood that the above description and the related figures are only intended to illustrate the present invention. Thus, the invention is not restricted to only the embodiments described above or stated in the Claims, but instead many different variations and adaptations of the invention, which are possible within the scope of the inventive idea defined in the accompanying Claims, will be obvious to one versed in the art.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A method for qualitative and quantitative detection of analytes, wherein an elongated migration base including an area for binding a magnetically marked analyte is used in the detection of an analyte in a sample, the method including the steps of:
   receiving the sample on the migration base;
   allowing the sample to spread on the migration base into the said area;
   arranging a receiving coil that is operated by alternating current having at least one set frequency fed to at least one driver coil;
   arranging the migration base in connection with the receiving coil; and
   detecting a change in inductance from the said frequency of the receiving coil in the presence of the sample wherein said change in inductance correlates to the amount of the magnetically marked analyte in the sample;
   wherein the said receiving coil is one of a set pair of receiving coils which are galvanically connected to each other and said set pair of receiving coils and driver coil are placed one inside an other.

2. A method according to claim 1, characterized in that the said set pair of receiving coils are an astatically set pair of receiving coils, over which alternating current fed to a driver coil induces voltage over the set pair of coils in the presence of a magnetically marked analyte in the sample.

3. A method according to claim 1, characterized in that the migration base of the sample is a porous strip.

4. A method according to claim 1, characterized in that the migration base of the sample is one of a plate or a capillary tube.

* * * * *